United States Patent
Chahal et al.

(12)

(10) Patent No.: US 11,619,573 B2
(45) Date of Patent: Apr. 4, 2023

(54) TEST METHOD FOR EVALUATING TEXTILE FABRIC PERFORMANCE

(71) Applicant: Target Brands, Inc., Minneapolis, MN (US)

(72) Inventors: Rajneet Kaur Chahal, North Oaks, MN (US); Avinash Shyamsarup Bhatnagar, Apple Valley, MN (US)

(73) Assignee: Target Brands, Inc., Minneapolis, MN (US)

( * ) Notice: Subject to any disclaimer, the term of this patent is extended or adjusted under 35 U.S.C. 154(b) by 0 days.

(21) Appl. No.: 17/498,034

(22) Filed: Oct. 11, 2021

(65) Prior Publication Data

US 2022/0026327 A1    Jan. 27, 2022

Related U.S. Application Data (62) Division of application No. 16/367,424, filed on Mar. 28, 2019, now Pat. No. 11,175,208.

(60) Provisional application No. 62/649,832, filed on Mar. 29, 2018.

(51) Int. Cl.
*G01N 3/56* (2006.01)
*G01N 33/36* (2006.01)

(52) U.S. Cl.
CPC .............. *G01N 3/56* (2013.01); *G01N 33/367* (2013.01)

(58) Field of Classification Search
CPC ................................ G01N 3/56; G01N 33/367
See application file for complete search history.

(56) References Cited

U.S. PATENT DOCUMENTS

| | | |
|---|---|---|
| 2005/0186872 A1 | 8/2005 | Wang et al. |
| 2017/0073859 A1 | 3/2017 | Cantin et al. |
| 2019/0301989 A1 | 10/2019 | Chahal et al. |

FOREIGN PATENT DOCUMENTS

| | | | |
|---|---|---|---|
| JP | 2007021604 A | * | 2/2007 |
| JP | 2015127369 A | * | 7/2015 |

OTHER PUBLICATIONS

English Machine Translation of Niikura et al., JP 2015127369 A, Jul. 9, 2015 (Year: 2015).*
English Machine Translation of Ito et al., JP 2007021604 A, Feb. 1, 2007 (Year: 2007).*

(Continued)

*Primary Examiner* — David Z Huang
(74) *Attorney, Agent, or Firm* — Amanda M. Prose; Westman, Champlin & Koehler, P.A.

(57) ABSTRACT

A method evaluating a strength of a textile for use in articles of clothing representative of normal wear and tear and comprising testing samples including the textile treated with an application of polyethylene, the untreated textile, and/or the textile being washed and dried one or more times; and/or where the textile has been conditioned. Each sample tested is weighed prior to and after abrasion resistance testing is conducted on each sample. The samples are each abraded with an abrasion resistance testing machine that has been modified with ISO test heads and an abrasive surface having a plurality of abrasion layers thereon. A number of rubs of abrasion between the abrasive surface and the test sample is pre-selected such that the test is run until the selected number of rubs have been completed. A bursting strength test can be further conducted on abraded areas of the testing samples.

9 Claims, 6 Drawing Sheets

(56) References Cited

OTHER PUBLICATIONS

Operator's Guide Sock Abrasion Kit Abrasion Resistance for Hosiery Modified Martindale Method According to EN 13770—Method 1, 2017, James H. Heal & Co Ltd (Year: 2017).*
Operator's Guide Martindale Abrasion and Pilling Testers the 1300 Series, James H. Heal & Co. Ltd, pp. 1-34, 2014.
Jerkovic et al., Study of the abrasion resistance in the upholstery of automobile seats, AUTEX Research Journal, vol. 10, No. 1, pp. 14-20, 2010.
Prosecution history of corresponding U.S. Appl. No. 16/367,424 including: Office Action dated May 5, 2021, Examiner Interview Summary dated Jun. 25, 2021, Amendment dated Jul. 8, 2021, Examiner Interview Summary dated Aug. 20, 2021 and Notice of Allowance dated Aug. 20, 2021.

* cited by examiner

| Sample Description | 0 HL Control before Abrasion Average | 0 HL Control after abrasion Average | Weight loss% | 3 HL Control before Abrasion Average | 3 HL Control after abrasion Average | Weight loss% | 5 HL Control before Abrasion Average | 5 HL Control after abrasion Average | Weight loss% | 30 HL Control before Abrasion Average | 30 HL Control after abrasion Average | Weight loss% |
|---|---|---|---|---|---|---|---|---|---|---|---|---|
| Jersey, CM 30s/1+SP30D, 220 gsm | 58 | 55 | 6.30% | 57 | 55 | 4.70% | 53 | 49 | 7.50% | 53 | 49 | 7.60% |
| Jersey, CM 30s/1+SP40D, 220 gsm | 59 | 55 | 6.20% | 55 | 52 | 5.40% | 56 | 52 | 7.70% | 53 | 50 | 5.00% |
| Jersey, CMRS 30s/1+SP30D, 220 gsm | 62 | 48 | 23.50% | 59 | 55 | 7.30% | 62 | 38.3 | 38.17% | 66 | 34 | 48.50% |
| Jersey, 24s/1+SP28D, 220 gsm | 80 | 54 | 32.10% | 80 | 52 | 35.40% | 80 | 50 | 37.50% | 80 | 44 | 44.60% |
| Specialty Jersey, Toughtex, 26s/1 Cotton+70d Span, 280 gsm | 44 | 45 | | 37 | 41 | | 36 | 39 | | 38 | 39 | |
| French Terry, CM 30S/1 + P150D + SP30D, 220 gsm | 88 | 49 | 44.3 | 88 | 48 | 45.8 | 95 | 49 | 54.7 | 92 | 40 | 56.5 |
| French Terry, 69%Cotton28%Poly 3%Span, 220 gsm | 91 | 69 | 24.5 | 91 | 68 | 25.6 | 91 | 68 | 25.5 | 96 | 68 | 24.4 |

FIG. 5

| Sample Description | 0 HL Treated before Abrasion Average | 0 HL Treated after abrasion Average | Weight loss% | 3HL Treated before Abrasion Average | 3HL Treated after abrasion Average | Weight loss% | 5 HL Treated before Abrasion Average | 5HL Treated after abrasion Average | Weight loss% | 30HL Treated before Abrasion Average | 30HL Treated after abrasion Average | Weight loss% |
|---|---|---|---|---|---|---|---|---|---|---|---|---|
| Jersey, CM 30S/1+SP30D, 220 gsm | 49 | 47 | 4.10% | 47 | 46 | 2.80% | 47 | 45 | 4.20% | 47 | 45 | 4.38% |
| Jersey, CM 30S/1+SP40D, 220 gsm | 44 | 41 | 5.30% | 43 | 41 | 4.70% | 42 | 39 | 6.30% | 42 | 40 | 4.00% |
| Jersey, CM RS 30S/1+SP30D, 220 gsm | 66 | 53 | 18.80% | 66.3 | 63 | 5.80% | 61 | 50 | 19.02% | 62 | 52 | 16.32% |
| Jersey, 24S/S+SP30D, 220 gsm | 68 | 53 | 22.20% | 71 | 54 | 24.30% | 69 | 53 | 26.05 | 73 | 53 | 30.60% |
| Specialty Jersey, Toughtex, 26S/1 Cotton+70d Span, 280 gsm | 43 | 50 | | 40 | 46 | | 37 | 38 | | 37 | 37 | |
| French Terry, CM30S/1 + P150D + SP30D, 220 gsm | 82 | 53 | 35.2 | 83 | 54 | 34.3 | 83 | 51 | 37.9 | 76 | 49 | 35.1 |
| French Terry, 69%Cotton28%Poly3%Span, 220 gsm | 84 | 71 | 14.7 | 83 | 71 | 14.4 | 82 | 70 | 14.2 | 81 | 70 | 13.6 |

FIG. 6

TEST METHOD FOR EVALUATING TEXTILE FABRIC PERFORMANCE

CROSS-REFERENCE OF RELATED APPLICATION

The present application is a divisional of and claims priority of U.S. patent application Ser. No. 16/367,424, filed Mar. 28, 2019, which is based on and claims the benefit of U.S. provisional patent application Ser. No. 62/649,832, filed Mar. 29, 2018, the content of which is hereby incorporated by reference in its entirety.

BACKGROUND

Evaluating the performance, or strength, of a textile involves subjecting the textile fabric to abrasion testing and continuing abrasion testing the sample until the textile fails, and the fibers break creating a hole in the textile. Textiles are finished with an application of a polyethylene (PE) coating to improve the resistance of the textile to abrasion, preventing textile failure and prolonging the life of the textile when the textile is incorporated into articles of clothing.

Generally, the prior testing methods for evaluating textile strength include subjecting the textile to abrasion testing by rubbing the sample with an abrading material such as duck cloth and continuing to rub the sample until the fibers break and a hole in the textile is formed. The strength of a textile having the PE coating thereon, a treated textile, is evaluated based on the total number of passes or rubs completed before textile failure occurs. The prior testing methods for evaluating the textile performance produced widely inconsistent results for abrasion resistance, thus providing an inaccurate indication of textile strength that is not consistent with articles returned to manufacturers for early and/or excessive wear and tear.

The discussion above is merely provided for general background information and is not intended to be used as an aid in determining the scope of the claimed subject matter. The claimed subject matter is not limited to implementations that solve any or all disadvantages noted in the background.

SUMMARY

A method of evaluating a textile for strength includes preparing one or more samples of a textile for abrasion resistance testing. The one or more samples include one or more of the textile treated with an application of polyethylene, the untreated textile, and the textile being washed and dried one or more times prior to testing. The abrasion resistance testing includes abrading each of the one or more samples using a controlled abrasion resistance test carried out for a pre-selected number of rubs of abrasive contact between each of the one or more samples and an abrading material. The test is carried out using an abrasion testing machine. Evaluating the strength of the textile for strength or performance in articles of clothing includes an evaluation based on the condition of the sample after abrasion testing, include the textile ability to withstand abrasion.

In another aspect of the present disclosure, each sample is weighed to obtain a first and a second weight measurement where the first weight measurement is obtained prior to abrasion resistance testing and the second weight measurement is obtained after completion of the abrasion resistance testing. Evaluating the strength of the textile for strength or performance in articles of clothing includes then a comparison of the first weight measurement and the second weight measurement across the one or more samples.

In accordance with a further embodiment, the abraded samples are subjected to burst strength testing. An abraded area of each sample is loaded into a burst strength testing machine and the burst strength of the fabric is obtained.

A method of testing the textile for abrasion resistance comprises preparing a plurality of samples of the textile for abrasion testing. An abrasion resistance testing machine is outfitted with a plurality of test heads to accommodate multiple samples for testing. A first pad is mounted to a bottom disk which corresponds to a test head. A second pad is then secured to, or on top of, the first pad wherein the second pad has an abrading surface. The first pad and the second pad are generally comprised of different materials having different abrading qualities. The abrading surface of the second pad is outwardly or upwardly facing and positioned for contacting the textile sample, which is secured to a top disk corresponding to each bottom disk of each test head. A plurality of selected parameters for testing, such as a speed of movement of the plurality of test heads, a testing weight for each test head, and/or a number of rubs for movement of the plurality of test heads are set and the samples are then abraded.

In accordance with a further embodiment, a method of preparing a plurality of samples of textiles for textile strength evaluation comprises cutting a plurality of test sample sets. Each test sample set includes a first sample and a second sample of the textile. The first sample may be the textile having an application of polyethylene thereon and the second sample would then be a control sample, without the application of polyethylene. One or more test sample sets are washed and dried at least once and a plurality of test sample sets are also washed and dried a plurality of times. The samples may also be conditioned prior to sample preparation.

The plurality of test sample sets include the textile in various states, such that in combination with abrasion resistance testing, the method of evaluating the strength of the textile is representative of user wear and tear when the textile is incorporated into articles of clothing.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DETAILED DESCRIPTION

Textile strength evaluation methods have not been able to consistently or cost effectively measure a textile performance beyond the failure of the material from a breakage of strands of the material and the formation of holes in the textile. Textiles for use in articles of clothing may frequently have a polyethylene ("PE") coating applied thereto to increase the strength of the textile and its resistance to abrasion, thus reducing the likelihood the article of clothing will begin to pill and eventually develop holes from wear and use.

In the past, the strength of a textile was evaluated by comparing the number of cycles of abrasion testing the finished textile (e.g., PE coated) could withstand before a hole is worn in the sample. Abrasion resistance testing machines, such as a Martindale abrasion testing machine can be used for subjecting textiles to abrasion. The abrasion resistance test, also referred to as a "rub test" is intended to simulate natural wear on a textile, where the textile sample is rubbed against a standard abrasive surface, such as a duck cloth, with a specified force. A Martindale testing machine is a standard machine used for testing and quantifying the abrasion resistance of a material. The number of abrasion cycles that are completed leading to the material being worn to a specified degree (e.g., pilling or a hole) with the Martindale testing is a "wear number." One cycle is equal to sixteen (16) rubs where a rub is a completed pass along a travel path such as an orbital path returning to a start point. The higher the wear number, generally the longer a material will resist abrasion.

Samples of the finished textile and samples of the control textile have been subjected to an open-ended number of rubs. That is, the abrasion test is run until a hole is formed in the sample. The wear number has been found to vary greatly, even among repeated samples of the same treated or control textile. The wear numbers are so inconsistent as to provide little insight as to the actual strength of the textile.

Embodiments described below improve the method of evaluating and testing strength of textiles, including PE coated textiles. The methods of testing and evaluation, as well as sample preparation described herein have significantly increased the consistency of the abrasion resistance results and reproducibility of the results, providing a representative strength evaluation of the textiles. The methods of testing and evaluation further produce a significant cost savings to manufacturers by reduction in the extent of testing required for evaluating the strength of the textiles. This cost savings is passed onto the consumer who also benefits by purchasing an article of clothing able to withstand repeated wear and use.

The PE coated textiles are treated textiles. Textiles are subjected to at least one coating of PE to increase a "wear strength" of the textile without adding weight to the textile. The PE coating acts to reinforce the knit fibers in the textile. The term "wear strength" as used herein refers to the ability of the textile to withstand user wear and tear when the textile is incorporated into an article of clothing. The wear strength includes the resistance of the textile to pilling (the formation of small balls of fluff on a knit fabric surface) and tearing from, user wear.

The treated textiles are subjected to abrasion resistance testing for purposes of evaluating the wear strength of the textile, also referred to herein after as a "strength" test and/or evaluation.

In accordance with one embodiment, an accurate and representative reflection of the wear strength of the treated textile from user wear, is achieved by subjecting a treated textile sample to a preselected number of abrasive rubs, using a modified abrasion resistance machine and test method, and further optionally comparing the weight of the material before and after the abrasion testing. The abraded textile samples are then be subjected to burst strength testing for further evaluation of the strength of the abraded fibers in the textile samples where the textile sample survived the abrasion test intact (e.g., without hole formation).

It is within the scope of this disclosure that embodiments of the methods described herein may further include the treated textile further evaluated for strength by a comparison of the treated textile performance to a control textile performance. A control sample may be a sample of the textile without a PE coating.

Further increasing the accuracy of the strength evaluation includes washing and drying the textile samples a number of times before abrasion testing to reflect user wear over time and after laundering the articles of clothing. The method described herein provides abraded textiles that are representative of the articles incorporating the textiles therein, and more accurately predicts textile failure from everyday wear and tear.

Burst strength testing is a fabric performance test method that measures the resistance of textile fabrics to bursting ("burst strength") using a hydraulic or pneumatic diaphragm bursting testers. Due to the construction of knit fabrics and their stretchable nature, it is not possible to measure the tensile strength of a knit fabric (e.g., by pulling it apart) or the tear strength (e.g., by attempting to tear the fabric). The burst strength test is carried out by using an inverted diaphragm to "poke" a hole in the textile sample. In the methods of testing and evaluating the textile strength described herein, the bursting strength test provides an indication of the decrease in fabric strength resulting from the abrasion testing of the samples. Theoretically, a textile coated with PE should have minimal to no loss in weight or bursting strength as the PE coating is applied to reduce the fiber loss resulting from wear (abrasion) and washing.

The methods described herein are used to test and evaluate the strength of cotton-rich textiles or fabrics treated with an application or coating of polyethylene. The terms "textile" and "fabric" are interchangeably used herein. For example, this method may be used with cotton fabrics, including but not limited to cotton blends such as cotton spandex, cotton polyester, or cotton polyester spandex blends. These textiles are then used to produce articles of clothing. The cotton-rich textiles are also treated or finished with an application of at least one layer of polyethylene (hereinafter referred to as "PE") to increase the strength of the textile for wear and use.

Figure 1:
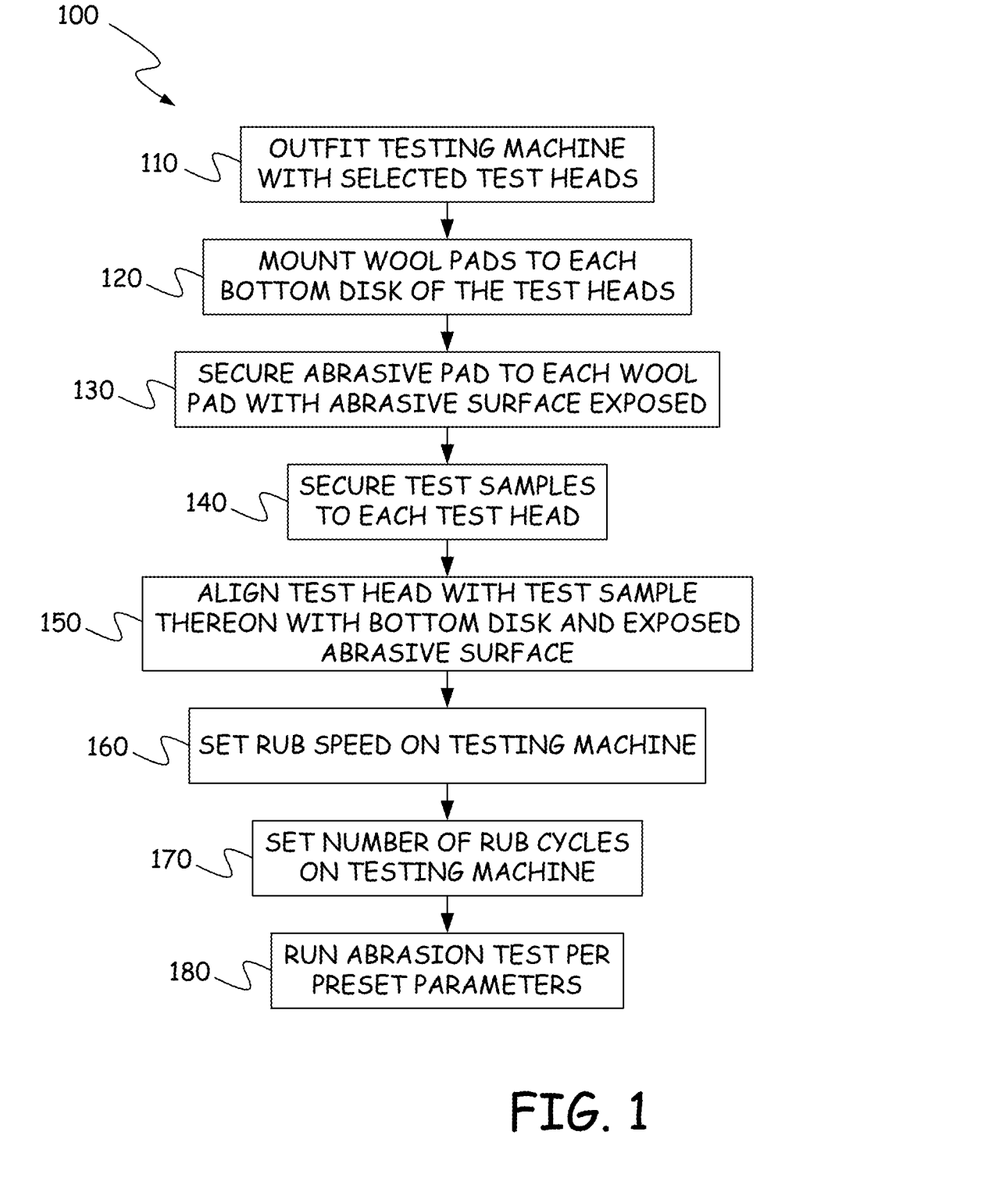
FIG. 1 is a flow diagram of a method of performing a modified abrasion test on one or more sample textile fabrics.

FIG. 1 provides a flow diagram for an abrasion test method according to an embodiment described herein. Textile samples subjected to this abrasion test may then be evaluated as described further below. The abrasion test method as described herein comprises subjecting one or more samples of a treated textile, and optionally its corresponding control textile sample, with an improved abrasion resistance test method. The abrasion test method can be used with the method of evaluating the textile for weight loss due to abrasion and burst strength as described in further detail below.

The abrasion test of the embodiment described herein includes modifying a standard abrasion testing apparatus for operating the abrasion test. The abrasion test also produces wear and tear in the textiles representative of user wear when the textile is incorporated into articles of clothing by running the test to a pre-selected number of abrasion "rubs" applied to the textile samples.

The abrasion test is carried out with a testing material which has an abrasive surface for contacting the textile during the abrasion test. The abrasive surface is generally provided on an abrasive pad and may have an increased coefficient of friction with the fabric as compared to prior abrasion testing materials.

Additional weight may be added to testing heads to provide additional force to the contact between the textile sample surface and the abrasive surface during testing.

In further detail, the embodiment described in FIG. 1, is a method 100 of abrasion testing which utilizes a standard abrasion testing machine. In the embodiment described herein a Martindale abrasion and pilling testing machine is used, however, it is contemplated that the embodiments described herein can be utilized on alternative abrasive testing machines.

As noted previously, the abrading surface in the prior art abrasion test methods is a duck fabric or duck cloth, such as a #10 cotton duck fabric. However, in one embodiment described herein, an abrasive material having a precise surface of micro-replicated structures such as triangular shaped abrading structures is used. The abrading surface has a higher coefficient of friction than duck cloth. Further, the abrasive material utilized in one such embodiment is an abrasive material having multiple layers of abrading structures which increase the abrasive life of the material. An example of an abrasive material used herein includes self-adhesive abrasive pads suited for sanding operations, namely with respect to composite and/or woodworking materials. In one particular embodiment, the abrasive surface is an abrasive pad having micron-sized abrasive pyramids such as the abrasive pads manufactured by 3M Company and identified as the Trizac™ Hookit™ Film Disc 268XA.

The Martindale abrasion tester is outfitted with selected testing heads at step 110. In the embodiment described herein, the abrasion tester is outfitted with ISO Martindale 90MM heads, having a top plate and a bottom disk. A wool pad is mounted on this bottom disk per ASTM D4966-12 (2016) standards at step 120. The abrasive pad is then secured onto the wool pad at step 130. The abrasive pad may be secured to the wool pad by an adhesive layer between the wool pad and the abrasive pad, allowing the abrasive surface of the pad to be exposed for contacting the textile sample during testing. When selecting the abrasive pad for adhering to the wool pad, abrasive pads having seams or other visible imperfections, such as multidirectional grain across the pad should be discarded.

The textile samples for testing, prepared as described in further detail below and referred to as disks or sample disks, are then mounted to the heads at step 140. In accordance with one embodiment, each sample is adhered to a surface of a corresponding head. At step 150, the head with the sample on it is aligned for contact with the abrasive surface of the abrasive pad below the head. The disks should each be substantially taught on the tester head without wrinkles or air bubbles between the disk and the tester head surface. The Martindale tester should be assembled to ensure that there is contact between the abrasive pad and the textile disk adhered on the top head.

A weight for providing force to the abrasion test is selected by test head weight alone or in combination with additional weight added to the test heads to increase the force behind the contact between the abrading surface and the test sample. In accordance with one embodiment, the heads have a weight sufficient to produce 9 kPa of pressure between the sample and the abrading surface during the abrasion test. Additional weight is added to the heads to exceed the 9 kPa of pressure. Auxiliary weight is added to a pilling plate in order to provide a more even distribution of abrasion and sufficient abrasion across the whole textile sample surface on the head. For example, an additional 415 grams of weight may be added in the form of a steel plate that is part of the ISO test method being positioned on top of the top head. The steel plate has a weight of about 415 grams per square meter ("GSM").

The abrasion resistance testing machine is set to a "pilling" operating function which includes a rub path having a variety of curves (e.g., 24 mm Lissajous motion) and a rub speed for the testing is set at step 160 and a number of rubs is then set at step 170. The rub speed indicates the relative speed between the abrasive surface and the sample. In accordance with one embodiment, all of the Martindale heads having the sample disks are set to the same preselected number of rubs at step 170. In the embodiment described herein, the abrasion resistance testing machine is set to an optimal number of rubs for each head in use for purposes of evaluating burst strength of the textile with consistency and accuracy. For example, in one embodiment, the number of rubs is in the range of approximately 4,500 to 6,000 rubs, or in the range of 5,000 to 5,500 rubs, or in the range of 5,100 to 5,300 rubs. In one embodiment described herein, approximately 5,120 rubs with the abrasive pad described has been found to provide abrasion or wear to the textile samples representative of user wear and tear. After the selected number of rubs between the abrasive pads and the fabric have been completed the initial test is completed at step 180.

Figure 2:
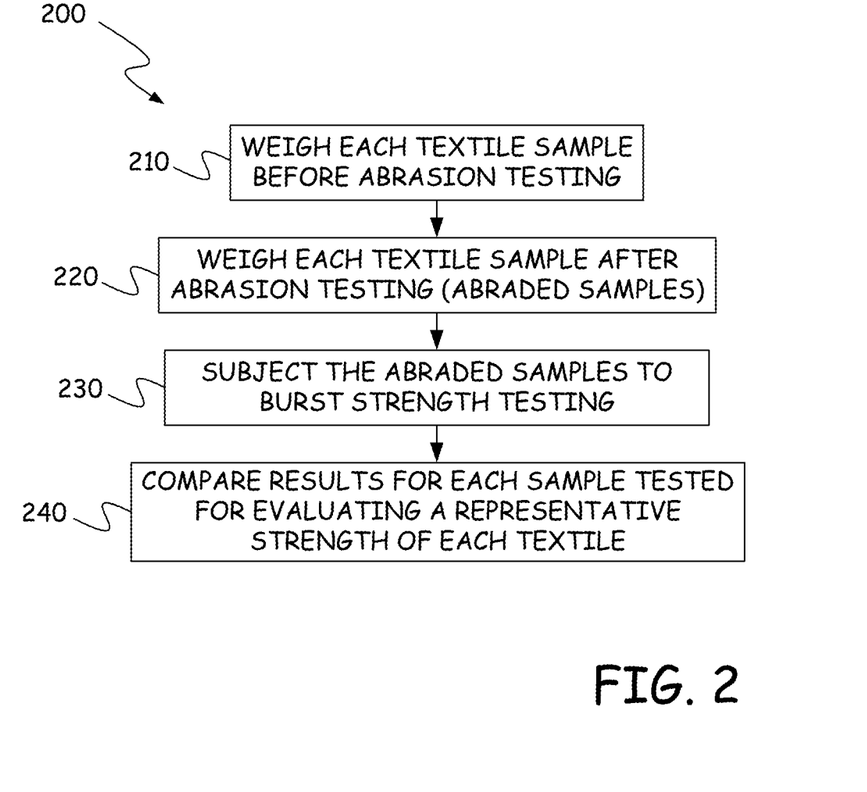
FIG. 2 is a flow diagram of a method of evaluating the samples subjected to an abrasion test for determining strength of the textile fabric.

FIG. 2 provides a flow diagram for a method of evaluating the strength of a treated textile 200 in accordance with one embodiment. The method comprises subjecting a treated, or finished, sample and optionally a corresponding control sample to abrasion testing as outlined in FIG. 1 and discussed above and then subjecting the treated sample and optionally the control sample to burst testing. The treated, or finished, sample is a textile having one or more layers of PE applied thereto. The corresponding control sample may be the same textile in an untreated state. While the methods described herein are used for evaluating the wear strength of a treated textile, the methods may also be used to evaluate the wear strength of untreated textile samples.

The evaluation of the treated textile may further include obtaining an initial weight of each sample at step 210. The samples are then subjected to the controlled abrasion testing of FIG. 1 described above. If the abraded sample failed prior to reaching the preselected number of rubs during the abrasion test, the number of rubs completed before failure occurred is recorded and assigned a failure code. For example, it can be noted for evaluation that the specified sample ruptured before the specified number of rubs. The samples may then be weighed again for obtaining a final weight of each abraded sample at step 220.

The abraded and/or weighed samples are each subjected to burst strength testing at step 230. The overall strength of the textile and thus its fitness for use in articles of clothing is evaluated by a comparison of the weight loss of the textile samples resulting from abrasion exposure at step 240. After abrasion testing, the burst strength of the treated textile and the control textile may be obtained and compared for further evaluating the strength of the textile. The change in sample weight can be attributed to textile fiber loss from pilling, thinning of the textile, tearing and/or the formation of holes in the textile, all of which negatively impact the durability of the textile for everyday wear and tear. The value of the negative change in weight (e.g., weight loss) correlates to wear strength, such that increased values of weight loss indicate a lower wear strength of the textile. These results may aid in selecting a textile, treated or untreated, for specific articles of clothing or areas of an article of clothing depending on the desired wear strength of the article.

To perform step 230, the abraded disks are mounted on a bursting strength tester machine for burst strength testing. A bursting strength tester is a machine utilizing forced air to determine the force require to burst or complete the rupture of the material and thus provides a quantified "burst strength" for the material. When testing the disks, the abraded area of the disk is positioned in a center circle of the burst tester and the burst testing machine is run to completion, where completion includes the textile sample having been burst completely. The actual burst strength observed for each disk is recorded for evaluating the strength of the textile after abrasion.

Figure 3:
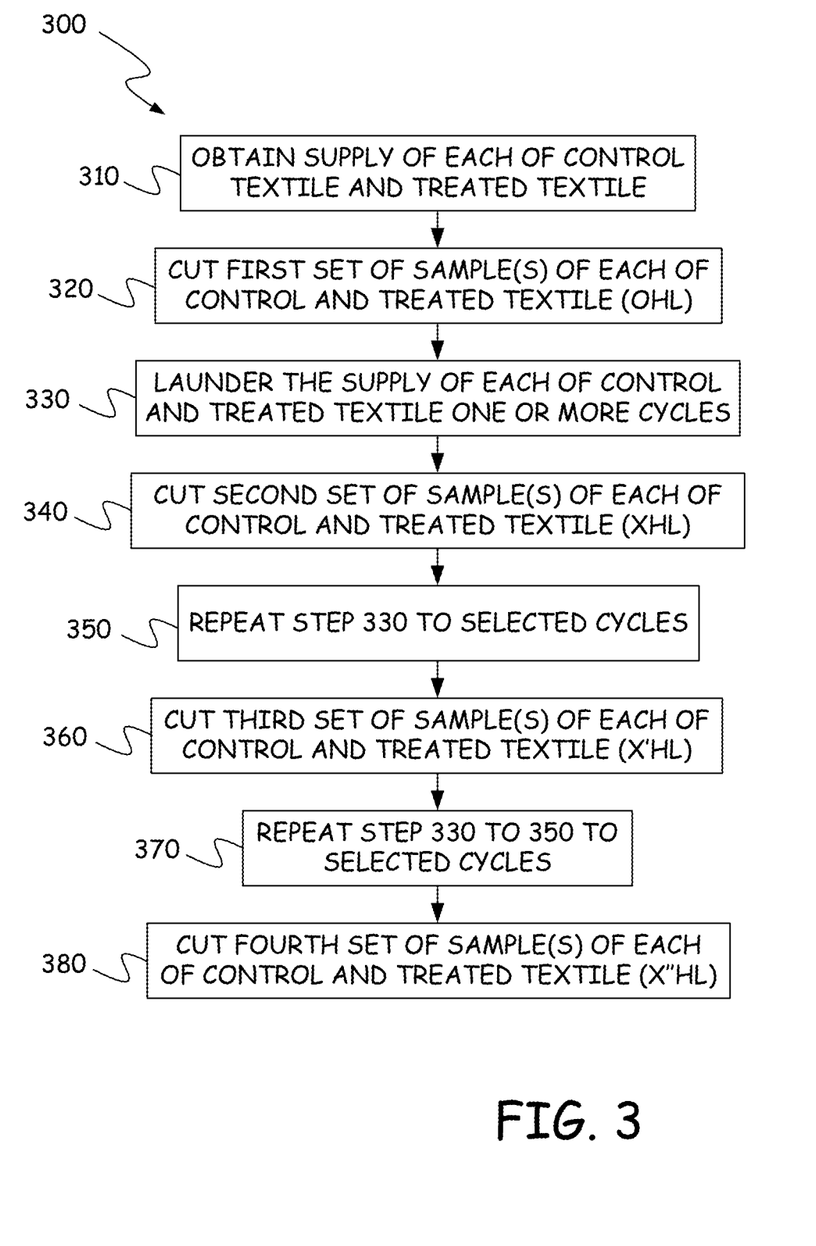
FIG. 3 is a flow diagram of a method of preparing the one or more sample textile fabrics for testing and evaluation of the textile fabric strength.
Figure 4:
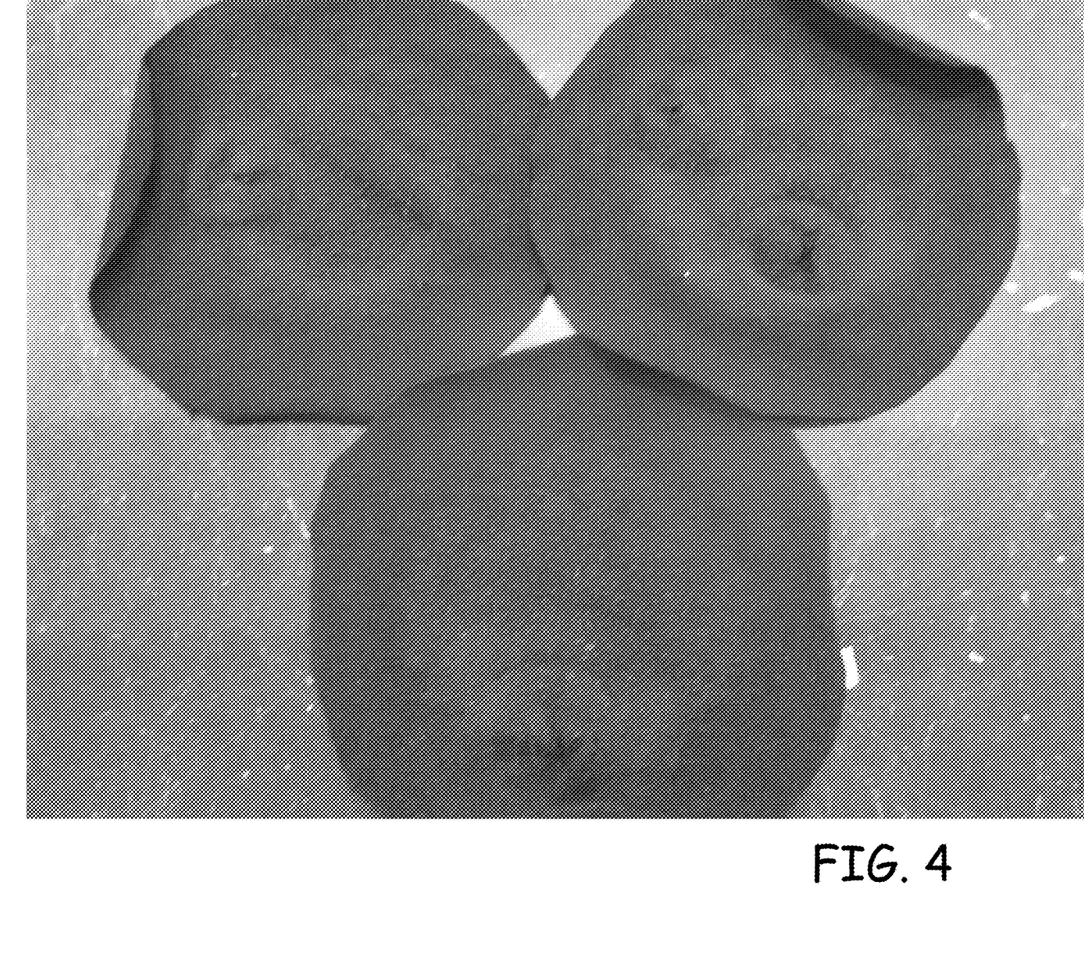
FIG. 4 is an image of abraded samples after conducting the abrasion test according to the embodiments described herein.

FIG. 3 provides a flow diagram for preparation of the textile samples 300 for testing and evaluation described herein. At step 310, a supply of both a treated textile and the corresponding control textile may be provided. The supply is sufficient to allow for multiple samples to be cut from each fabric for testing one or more conditions of the textile to evaluate the strength of the textile. The textile supplies may be conditioned or relaxed according to ASTM D4966 standards prior to preparation for testing.

The treated and control samples are prepared by cutting to size for compatibility with the testing machine. The treated and control samples are also prepared according to selected conditions as described below and are then labeled.

A cutter such as a die cutter may be used to cut samples of each of the control textile and the treated textile for testing. For example, a plurality of disks are cut from each supply of the provided control textile and treated textile. The plurality of disks of each of the control textile and the treated textile are cut to a size and geometry that matches the geometry of the top head of the tester in one embodiment. As described herein, the samples are cut to approximately 4" disks as the size of the top head is 3.54".

A first set of fabric samples is cut without washing the fabric and the samples are appropriately labeled at step 320.

At step 330, the remaining supplies of the treated textiles and optionally the control textiles are run through multiple laundering cycles, where one cycle is defined as washing and drying the fabric one time. In accordance with one embodiment, the sample textiles are washed and dried three (3) times during step 330. At step 340, a second set of samples of the treated textile and the control textile are cut from the laundered supply of treated textile and control textile. Continuing on at step 350, the supplies of control textiles and the treated textiles are then washed and dried an additional plurality of times, for example two additional times to bring the number of cycles to a total five (5) cycles. At step 360, a third set of samples of the treated textile and the control textile are cut from the further laundered supplies. At step 370, the remaining uncut supplies are washed again for a number of cycles. In accordance with one embodiment, the control textile and the treated textile are washed and dried for a total of thirty (30) cycles. At step 380, a fourth set of samples of treated textile and control textile is cut from the still further laundered supply produced at step 370.

Test reports are generated which compare the actual testing data gathered for each of the samples prepared and subjected to abrasion testing and burst strength testing. In one embodiment this may include both the control and treated textile samples as prepared and subjected to abrasion testing and burst strength testing. A control weight before abrasion, a control weight after abrasion and thus a weight loss per sample may be quantified as a percentage as well as the treated weight before and after abrasion, the change in weight quantified as a percentage.

The burst strength is also compared for each sample tested and a reduction in burst strength of the textile across selected conditions is compared. When evaluating the abraded samples for burst strength, an observed reduction in burst strength across the samples tested indicates a quality concern with the textile. A reduction in burst strength of the sample may indicate a potential textile quality issue. Textile samples that fail to meet pre-set performance standards with respect to burst strength after abrasion are not suitable for use in articles of clothing.

Evaluation of the fitness for use of the PE textile sample may include one or more of the following: the number of rubs the samples endured during abrasion testing, the weight of the sample before and after abrasion testing, the burst strength, or a comparison of the PE sample to its control sample in abrasion testing and burst strength.

Comparative Examples

Figure 5:
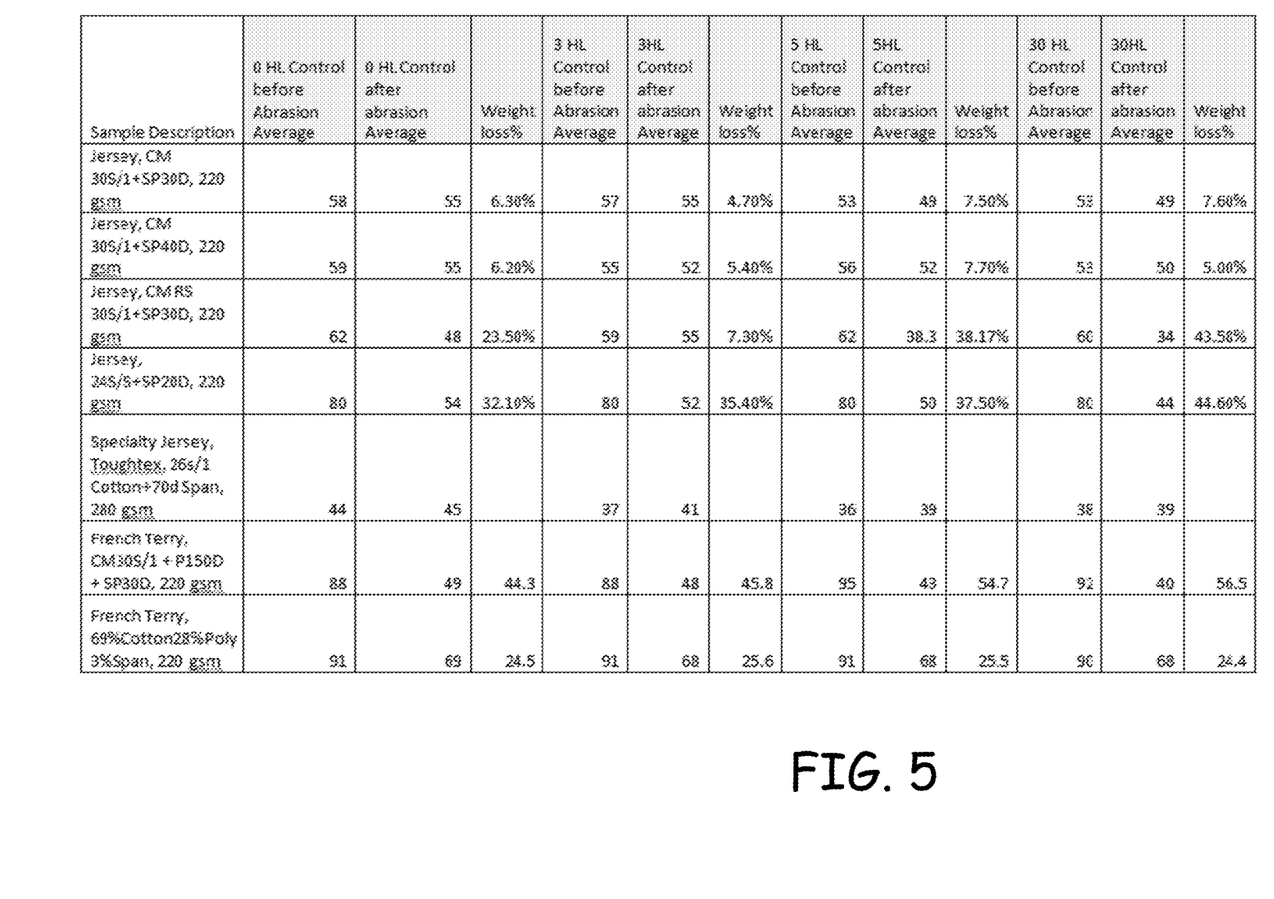
FIG. 5 is TABLE 1A showing results for selected textiles of the modified abrasion test described herein.
Figure 6:
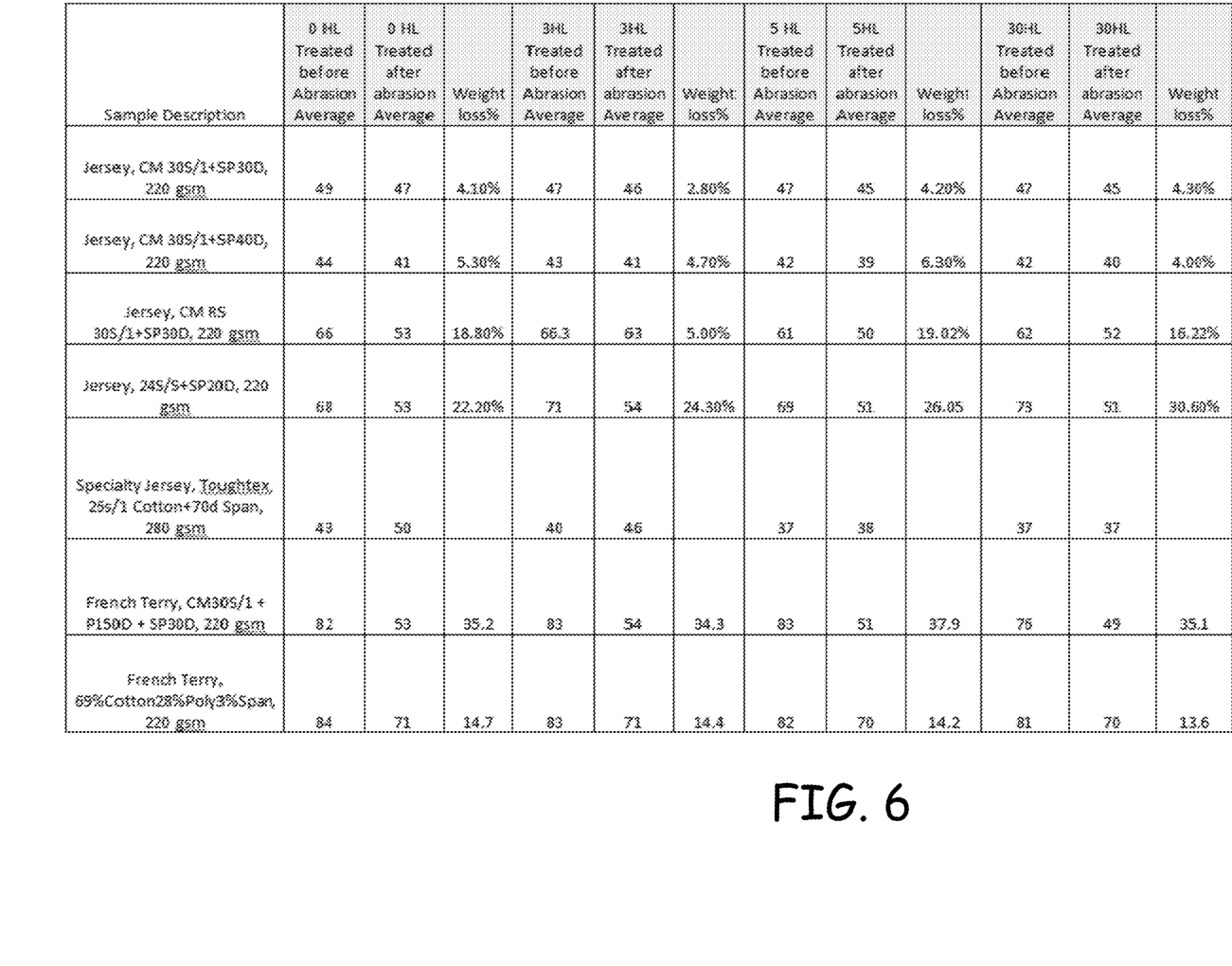
FIG. 6 is TABLE 1B showing results for treated textiles of the modified abrasion test described herein.

Referring to FIGS. 5-6, TABLE 1A displays the abrasion test results of various fabric textiles including different jersey fabric textiles and French terry cloth textiles, subjected to abrasion resistance testing according to the embodiment described herein. The results in TABLE 1A are average weights per a plurality of samples tested. Averages are reported for purposes of illustration. TABLE 1B displays the abrasion test results of the various fabric textiles including different jersey fabric textiles and French terry cloth textiles having a PE coating thereon and, subjected to abrasion resistance testing according to the embodiment described herein. The results in TABLE 1A are average weights per a plurality of samples tested. Averages are reported for purposes of illustration.

TABLE 2 displays the burst strength test results of the jersey fabric textile subjected to abrasion resistance testing according to the embodiment described herein. The textile tested is jersey fabric classified as CM 30S/1+SP30D jersey fabric having a weight of 220 grams per square meter (GSM). The textile samples below were prepared according to the method 300 described herein, tested according to the test method 100 described herein and evaluated according to the method 200 also described herein. The samples include a plurality of control and treated textile samples prepared and tested where the samples were tested as provided (e.g. 0 HL), after three cycles of washing and drying (3 HL), after 5 cycles of washing and drying (5 HL) and after 30 cycles of washing and drying (30 HL). The samples were weighed prior to abrasion testing and after completion of 5,120 rubs.

TABLE 2

| RUN ID | Burst Strength (kPa) before Abrasion | Burst Strength (kPa) before Abrasion Average | Burst Strength (kPa) after abrasion | Burst Strength (kPa) after abrasion Average |
|---|---|---|---|---|
| 0 HL | 55 | 58 | 55 | 55 |
| CONTROL | 62 | | 55 | |
| (3 SAMPLES) | 58 | | 54 | |
| 3 HL | 58 | 57 | 54 | 55 |
| CONTROL | 55 | | 55 | |
| (3 SAMPLES) | 59 | | 55 | |
| 5 HL | 53 | 53 | 50 | 49 |
| CONTROL | 54 | | 48 | |
| (3 SAMPLES) | 53 | | 50 | |
| 30 HL | 52 | 53 | 49 | 49 |
| CONTROL | 53 | | 47 | |

TABLE 2-continued

| RUN ID | Burst Strength (kPa) before Abrasion | Burst Strength (kPa) before Abrasion Average | Burst Strength (kPa) after abrasion | Burst Strength (kPa) after abrasion Average |
|---|---|---|---|---|
| (3 SAMPLES) | 53 | | 50 | |
| 0 HL TREATED (3 SAMPLES) | 50 | 49 | 46 | 47 |
| | 48 | | 47 | |
| | 48 | | 47 | |
| 3 HL TREATED (3 SAMPLES) | 48 | 47 | 46 | 46 |
| | 45 | | 44 | |
| | 48 | | 47 | |
| 5 HL TREATED (3 SAMPLES) | 48 | 47 | 47 | 45 |
| | 50 | | 46 | |
| | 44 | | 43 | |
| 30 HL TREATED (3 SAMPLES) | 45 | 47 | 44 | 45 |
| | 49 | | 45 | |
| | 46 | | 45 | |

TABLE 3 displays the burst strength test results of the jersey fabric textile subjected to abrasion resistance testing according to the embodiment described herein. The textile tested is a CM 30S/1+SP40D jersey fabric having a weight of 220 GSM. The textile samples below were prepared according to the method 300 described herein, tested according to the test method 100 described herein and evaluated according to the method 200 also described herein. The samples include a plurality of control and treated textile samples prepared and tested where the samples were tested as provided (e.g. 0 HL), after three cycles of washing and drying (3 HL), after 5 cycles of washing and drying (5 HL) and after 30 cycles of washing and drying (30 HL). The samples were weighed prior to abrasion testing and after completion of 5,120 rubs.

TABLE 3

| RUN ID | Burst Strength (kPa) before Abrasion | Burst Strength (kPa) before Abrasion Average | Burst Strength (kPa) after abrasion | Burst Strength (kPa) after abrasion Average |
|---|---|---|---|---|
| 0 HL CONTROL (3 SAMPLES) | 57 | 59 | 53 | 55 |
| | 60 | | 57 | |
| | 60 | | 56 | |
| 3 HL CONTROL (3 SAMPLES) | 55 | 55 | 51 | 52 |
| | 53 | | 51 | |
| | 58 | | 55 | |
| 5 HL CONTROL (3 SAMPLES) | 55 | 56 | 51 | 52 |
| | 57 | | 51 | |
| | 57 | | 54 | |
| 30 HL CONTROL (3 SAMPLES) | 52 | 53 | 49 | 50 |
| | 52 | | 50 | |
| | 55 | | 52 | |
| 0 HL TREATED (3 SAMPLES) | 46 | 44 | 43 | 41 |
| | 41 | | 39 | |
| | 44 | | 42 | |
| 3 HL TREATED (3 SAMPLES) | 44 | 43 | 41 | 41 |
| | 41 | | 40 | |
| | 43 | | 41 | |
| 5 HL TREATED (3 SAMPLES) | 41 | 42 | 39 | 39 |
| | 43 | | 40 | |
| | 42 | | 39 | |
| 30 HL TREATED (3 SAMPLES) | 43 | 42 | 40 | 40 |
| | 43 | | 42 | |
| | 40 | | 38 | |

TABLES 4-7 below display the results of a prior art abrasion test applied to four different fabrics. The prior abrasion test conducted was the Standard Test Method for Abrasion Resistance of Textile Fabrics (e.g., "Martindale Abrasion Tester Method") run according to ASTM D4966-12(2016) standards and wherein the textile sample was rubbed until failure (fiber breakage, holes) occurred and strength is evaluated by the number of rubs until fiber breakage occurred. The wear number is recorded below for each sample.

TABLE 4 below reflects the wear number observed before a 220 GSM weight 95/5 cotton/span jersey textile, identified as Sample A, failed. This test was repeated with four disks of each textile sample and illustrates the inconsistency with the standard Martindale Abrasion Tester Method with respect to abrasion testing and strength evaluation.

TABLE 4

SAMPLE A 1RUN ID

| | WEAR NUMBER (RUBS UNTIL FAILURE (1-4)) | | | |
|---|---|---|---|---|
| 0 HL CONTROL (4 SAMPLES) | 467 | 467 | 700 | 1358 |
| 0 HL TREATED (4 SAMPLES) | 2533 | 1933 | 2200 | 2333 |
| 20 HL CONTROL (4 SAMPLES) | 333 | 400 | 300 | 417 |
| 20 HL TREATED (4 SAMPLES) | 1967 | 1500 | 2333 | 3433 |

TABLE 5 below reflects the wear number observed before a 220 GSM weight 90/7 cotton/spandex yarn dye textile, identified as Sample B, failed.

TABLE 5

SAMPLE B RUN ID

| | WEAR NUMBER (RUBS UNTIL FAILURE) |
|---|---|
| 0 HL CONTROL | 1167 |
| 0 HL TREATED | 3067 |
| 20 HL CONTROL | 417 |
| 20 HL TREATED | 3400 |

TABLE 6 below reflects the number of rubs observed before a 220 GSM weight 90/7 cotton/spandex printed textile, identified as Sample C, failed.

TABLE 6

SAMPLE C RUN ID

| | WEAR NUMBER (RUBS UNTIL FAILURE) |
|---|---|
| 0 HL CONTROL | 550 |
| 0 HL TREATED | 2167 |
| 20 HL CONTROL | 467 |
| 20 HL TREATED | 1500 |

TABLE 7 below reflects the wear number observed before a 220 GSM weight 93/7 cotton/spandex blend textile, identified as Sample D, failed.

TABLE 7

SAMPLE D RUN ID

| | WEAR NUMBER (RUBS UNTIL FAILURE) |
|---|---|
| 0 HL CONTROL | 300 |
| 0 HL TREATED | 1767 |
| 20 HL CONTROL | 318 |
| 20 HL TREATED | 1800 |

It can be seen that the methods described herein as used for testing and evaluating fabric for strength based in part on abrasion resistance and also burst strength provide increased consistency in the results of strength evaluation. This evaluation is more representative of actual user wear and tear when the textiles are incorporated into articles of clothing.

Although elements have been shown or described as separate embodiments above, portions of each embodiment may be combined with all or part of other embodiments described above.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms for implementing the claims.

What is claimed is:

1. A method of evaluating a textile for strength comprising:
    preparing one or more samples of a textile for abrasion resistance testing wherein the one or more samples comprise one or more samples of the textile with an application of polyethylene, and the one or more samples of textile being washed and dried one or more times;
    securing an abrasive surface directly on to a standard test pad installed on a test head of an abrasion resistance testing machine with an adhesive layer between the abrasive surface and the standard test pad and wherein the abrasive surface has a coefficient of friction greater than a coefficient of friction of the standard test pad and wherein the abrasive surface comprises micro-replicated abrading structures, multiple layers of abrading structures or combinations thereof;
    abrading each of the one or more samples with the abrasive surface instead of the standard test pad using an abrasion resistance test wherein the abrasion resistance test comprises applying a pre-selected number of rubs of abrasive contact with the abrasive surface to each of the one or more samples and adjusting one or more of a speed of movement of the test head and a force behind contact between the sample and the abrasive surface by increasing a weight of test head by addition of a weighted element on top of the test head;
    stopping the abrading of the sample if the sample develops a hole prior to reaching the pre-selected number of rubs of abrasive contact; and
    evaluating the one or more samples based in part on the number of rubs of abrasion contact the sample withstands before developing one or more holes.

2. The method of claim 1 and further comprising:
    weighing each of the one or more samples of textile to obtain a first weight measurement for each sample wherein the first weight measurement is obtained prior to abrasion resistance testing;
    weighing each of the one or more samples of textile to obtain a second weight measurement for each sample wherein the second weight measured is obtained after abrading; and
    comparing the first weight measurement to the second weight measurement for each of the one or more samples for evaluating the textile for strength.

3. The method of claim 1, and further comprising testing an abraded area of each of the one or more samples for a burst strength.

4. The method of claim 1, wherein the abrasion resistance test comprises rubbing an abrasive surface against a surface of each of the one or more samples of the textile, wherein the abrasive surface comprises multiple layers of abrasive structures thereon.

5. The method of claim 1, wherein the pre-selected number of rubs is in the range of 5,000 to 5,500 rubs.

6. The method of claim 5, wherein the pre-selected number of rubs is 5,120.

7. The method of claim 1, wherein preparing one or more samples further comprises:
    washing and drying at least one test sample a first number of wash and dry cycles;
    washing and drying at least a second test sample a second number of wash and dry cycles wherein the first number and second number of wash and dry cycles are different.

8. The method of claim 1, wherein the one or more samples are conditioned pursuant to ASTM D4966 prior to cutting.

9. The method of claim 1, wherein the textile is a cotton-rich fabric comprising cotton, polyester, spandex or blends thereof.

* * * * *